United States Patent [19]

Kirst et al.

[11] Patent Number: 4,487,923

[45] Date of Patent: Dec. 11, 1984

[54] METHOD OF PREPARING 23-MONOESTERS OF OMT AND DMT

[75] Inventors: Herbert A. Kirst; John E. Toth, both of Indianapolis, Ind.

[73] Assignee: Eli Lilly and Company, Indianapolis, Ind.

[21] Appl. No.: 475,271

[22] Filed: Mar. 14, 1983

Related U.S. Application Data

[63] Continuation of Ser. No. 330,295, Dec. 14, 1981, abandoned.

[51] Int. Cl.³ ............... C07H 1/00; C07H 17/08
[52] U.S. Cl. ..................... 536/7.1; 536/18.5; 536/115; 536/119
[58] Field of Search ............ 536/7.1, 115, 119, 7.2

[56] References Cited

U.S. PATENT DOCUMENTS

| | | | |
|---|---|---|---|
| 3,459,853 | 8/1969 | Gorman et al. | 424/121 |
| 3,598,806 | 8/1971 | Morozowich | 536/16.3 |
| 4,029,881 | 6/1977 | Inouye et al. | 536/9 |
| 4,092,473 | 5/1978 | Okamoto et al. | 536/17 |
| 4,141,971 | 2/1979 | Krausz et al. | 424/180 |
| 4,321,361 | 3/1982 | Baltz et al. | 536/17 R |
| 4,373,095 | 2/1983 | Ganguly | 536/7.1 |

FOREIGN PATENT DOCUMENTS 0033433  8/1981  European Pat. Off. ............ 536/7.1

OTHER PUBLICATIONS

Derwent, Abstract, 83-729999/32, of German Patent 3301-959-A, Aug. 4, 1983, assigned to Toyo Jozo K.K.
A. Tanaka et al., "Synthesis of Recyclized Macrolide Antibiotics and Related Derivatives from Mycaminosyl Tylonolide", *Bull. Soc. Chem. Soc. Japan 54*, 3837–3845, (1981).
A. Tanaka et al., "Synthesis of 4'-Deoxymycaminosyl Tylonolide", *J. Antibiotics 34*, 1374–1376, (1981).
A. Tanaka et al., "Syntheses of Derivatives of 4'-Deoxymycaminosyl Tylonolide and Mycaminosyl Tylonolide Modified at C-23", *J. Antibiotics 34*, 1377–1380, (1981).

*Primary Examiner*—Johnnie R. Brown
*Attorney, Agent, or Firm*—Nancy J. Harrison; Arthur R. Whale

[57] ABSTRACT

An improved method of preparing 23-monoester derivatives of 5-O-mycaminosyl tylonolide (OMT) and demycinosyltylosin (DMT) is provided. This method comprises esterifying the antibiotic with an acylating agent in the presence of an external base, such as pyridine or 2,4,6-collidine, until acylation of the 23-hydroxyl group is substantially complete, and separating the 23-monoester derivative. 23-Monoester derivatives of OMT and DMT are useful antibiotics and/or intermediates to antibiotics.

7 Claims, No Drawings

METHOD OF PREPARING 23-MONOESTERS OF OMT AND DMT

This application is a continuation of application Ser. No. 330,295, filed Dec. 14, 1981, now abandoned.

SUMMARY OF THE INVENTION

This invention relates to an improved method of preparing 23-monoester derivatives of 5-O-mycaminosyl tylonolide (OMT) and demycinosyltylosin (DMT) which comprises carrying out the esterification of OMT or DMT at low to room temperatures with an appropriately selected acylating agent in the presence of an external base such as pyridine or 2,4,6-collidine until acylation of the 23-hydroxyl group is substantially complete. The 23-monoesters of OMT are compounds of formula 1:

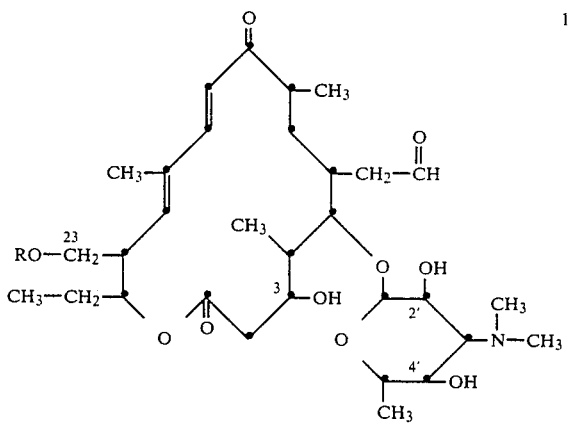

wherein R is a specified acyl group. The 23-monoesters of DMT are compounds of formula 2:

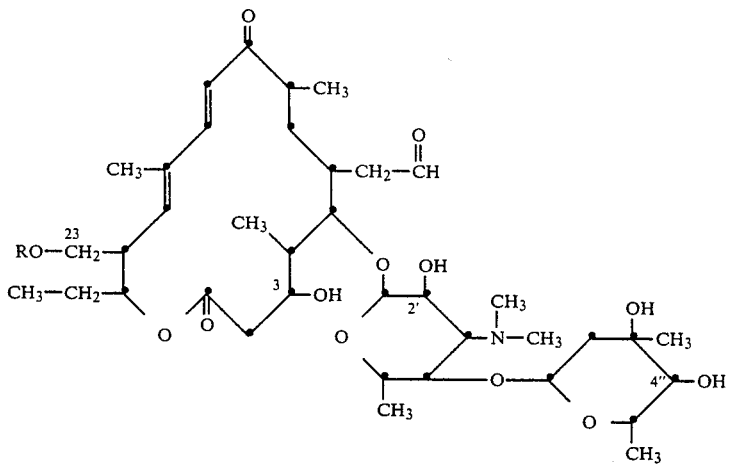

wherein R is a specified acyl group.

Previously, it was necessary to prepare 2',4',23-tri-O-acyl derivatives of OMT or 2',23-di-O-acyl derivatives of DMT and then remove the acyl groups at the 2',4'-positions of OMT or the 2'-position of DMT in order to prepare 23-monoester derivatives of OMT or DMT. The method of this invention provides a direct route whereby OMT or DMT can be selectively acylated on the 23-hydroxyl group to give the desired 23-monoester derivative.

The 23-monoester derivatives of OMT and DMT are useful antibiotics and/or intermediates to antibiotics.

DETAILED DESCRIPTION OF THE INVENTION

This invention relates to an improved method of preparing new antibiotics. In particular, this invention relates to a method of preparing the 23-monoester derivatives of OMT and DMT directly from OMT and DMT, respectively. This method comprises esterifying OMT or DMT with an appropriate acylating agent in the presence of an external base, such as pyridine or 2,4,6-collidine, until acylation of the 23-hydroxyl group is substantially complete.

23-Esters of OMT are described in the copending application of Herbert A. Kirst entitled OMT ESTER DERIVATIVES, Ser. No. 330,341, filed Dec. 14, 1981, now U.S. Pat. No. 4,401,660. The 23-monoester derivatives of DMT are described in the copending application of Herbert A. Kirst entitled DMT ESTER DERIVATIVES, Ser. No. 330,294, filed Dec. 14, 1981, now U.S. Pat. No. 4,396,613. The 23-monoester derivatives described in these applications are compounds of formulas 1 or 2 wherein R is an acyl group selected from:

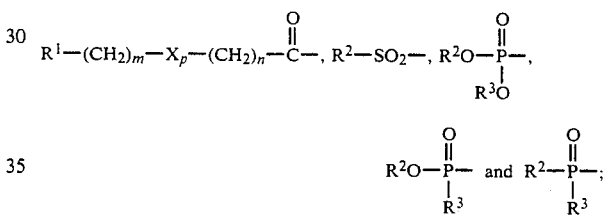

p is 0 or 1; m and n are integers from 0 to 4; $R^1$ is hydrogen, halo, $C_1$–$C_4$-alkyl, $C_3$–$C_8$-cycloalkyl, phenyl, $C_5$–$C_8$-cycloalkenyl, naphthyl, indenyl, tetralinyl, decalinyl, adamantyl, 1-ethyl-1,4-dihydro-4-oxo[1,3]dioxolo[4,5-g]cinnolin-3-yl (cinnoxacinyl), a monocyclic heterocyclic ring system comprising 3 to 8 atoms or a bicyclic heterocyclic ring system comprising 6 to 11 atoms, provided that at least 1 atom of the ring system is carbon and at least 1 atom of the ring system is a heteroatom selected from O, N, and S; and wherein $R^1$ and the connecting alkyl groups —(CH$_2$)$_m$— and —(CH$_2$)$_n$— are optionally substituted by one or two halo, methyl, ethyl, methoxy, amino, N-protected-amino, methylamino, dimethylamino, nitro, acetoxy, acetamido, azido, carbomethoxy, carboxamido, cyano, or hydroxyl groups, provided that, if the substituent is other than halo or alkyl, there can be no more than one substituent on any connecting —CH$_2$— group; X is O, S, —NH—, —N(CH$_3$)—, —C≡C—, —CH=CH—, —C(CH$_3$)=CH—, —CH=C(CH$_3$)— or —C(CH$_3$)=C(CH$_3$)— ; R$^2$ and R$^3$ are C$_1$-C$_5$-alkyl or optionally substituted phenyl or benzyl; and the acid addition salts thereof.

The terms "C$_1$-C$_4$-alkyl" and "C$_1$-C$_5$-alkyl" as used herein mean a straight- or branched-chain alkyl group containing from one to four or from one to five carbon atoms, respectively. In such a moiety, the alkyl group can optionally bear one to three halo substituents. Halo substituents are selected from the group consisting of Cl, Br and F. Such groups include methyl, ethyl, isopropyl, n-butyl, sec-butyl, isobutyl, tert-butyl, isovaleryl, chloromethyl, trichloromethyl and trifluoromethyl.

The term "optionally substituted phenyl or benzyl" means that the phenyl portion of the moiety is optionally substituted by from one to five halo or methyl or by from one to two methoxyl, nitro or hydroxyl groups.

The term "C$_3$-C$_8$-cycloalkyl" means a saturated ring having from three to eight carbon atoms in the ring. Examples of such rings are cyclopropyl, cyclobutyl, cyclopentyl, cyclohexyl, and cyclooctyl. By "C$_5$-C$_8$-cycloalkenyl" is meant a carbocylic ring which contains from five to eight carbon atoms and which also contains one or two double bonds. Cyclohexadienyl, cyclohexenyl, cyclopentenyl, and cyclooctadienyl are examples of such rings.

The term "monocyclic or bicyclic heterocyclic ring system" as used herein includes saturated or unsaturated heterocyclic moieties containing at least one carbon atom and at least one heteroatom selected from oxygen, nitrogen and sulfur. Heterocyclic groups contemplated include:

unsaturated 3 to 8-membered monocyclic groups, for example, pyrrolyl, Δ$^3$-pyrrolinyl, imidazolyl, pyrazolyl, pyridyl, pyrimidyl, pyrazinyl, pyridazinyl, triazinyl, triazolyl (e.g., 4H-1,2,4-triazolyl, 1H-1,2,3-triazolyl, etc.), tetrazolyl (e.g., 1H-tetrazolyl, 2H-tetrazolyl, etc.), oxazolyl, isoxazolyl, oxadiazolyl (e.g., 1,2,4-oxadiazolyl, 1,3,4-oxadiazolyl, 1,2,5-oxadiazolyl, etc.), thiazolyl, isothiazolyl, thiadiazolyl (e.g., 1,2,4-thiadiazolyl, 1,3,4-thiadiazolyl, 1,2,5-thiadiazolyl, etc.), thienyl, furanyl, etc;

saturated 3 to 8-membered monocyclic groups, for example, pyrrolidinyl, imidazolidinyl, piperidinyl, piperazinyl, morpholinyl, thiazolidinyl, tetrahydrofuranyl, tetrahydrothienyl, tetrahydropyranyl, dioxanyl, etc.;

unsaturated 6 to 11-membered bicyclic groups, for example, indolyl, isoindolyl, coumaronyl, benzothiofuranyl, benzimidazolyl, quinolyl, isoquinolyl, benzopyrazolyl, cinnolinyl, quinazolinyl, benzoxazolyl, benzothiazolyl, benzoxazinyl, coumarinyl, etc.; and the like.

"N-protected-amino" means that the amino group is substituted by a suitable protecting group. Such a group must be one which is compatible with the other functional groups in OMT or DMT and which can be readily removed from the 23-O-acylated derivative. One especially useful amino-protecting group is the tertbutoxycarbonyl (t-BOC) group.

When R is an acyl group wherein X is —CH=CH—, —C(CH$_3$)=CH—, —CH=C(CH$_3$)—, or —C(CH$_3$)=C(CH$_3$)— , the substituents on the double bond can be in either the cis or trans configuration.

Illustrative R groups include those wherein:

(1) R is

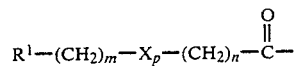

and (a) R$^1$ is hydrogen or C$_1$-C$_4$-alkyl;
(b) p is 0;
(c) R$^1$ is optionally substituted phenyl;
(d) X is oxygen or —NH— and n is 0; or
(e) X is oxygen or sulfur and n is 1; and (2) R is R$^2$—SO$_2$ and (a) R$^2$ is C$_1$-C$_5$-alkyl; or
(b) R$^2$ is optionally substituted phenyl.

OMT is prepared as described by Marvin Gorman and Robert B. Morin in U.S. Pat. No. 3,459,853, issued Aug. 5, 1969. DMT is prepared as described by Richard H. Baltz, Gene M. Wild, and Eugene T. Seno in their copending application entitled DEMYCINOSYL-TYLOSIN AND PROCESS FOR ITS PRODUCTION, Ser. No. 156,854, filed June 12, 1980, now U.S. Pat. No. 4,321,361. A preferred method of preparing OMT, by mild acid hydrolysis of DMT, is described by Baltz et al. in Ser. No. 156,854.

The method of this invention comprises esterifying OMT or DMT directly on the 23-hydroxyl group by carrying out the esterification with an appropriately selected acylating agent in the presence of an external base, such as pyridine or 2,4,6-collidine, until acylation of the 23-hydroxyl group is substantially complete. The extent of acylation is monitored by thin-layer chromatography (TLC). Additional acylating agent is added as necessary to complete acylation of the 23-hydroxyl group.

In the absence of external base, esterification of the 2'- and 4'-hydroxyl groups of OMT and of the 2'-hydroxyl group of DMT is more facile than esterification of the 23-hydroxyl group. The previous method of preparing 23-monoesters of OMT or DMT, therefore, involved (1) preparing a 2',4'-diacyl derivative of OMT or a 2'-O-acyl derivative of DMT, (2) esterifying these compounds on the 23-hydroxyl group, and (3) removing the 2',4'- or 2'-acyl group(s) to obtain the 23-monoester derivative. In the case of either OMT or DMT, therefore, a series of three reactions was required to obtain the 23-monoester derivative. The present invention provides a method whereby the 23-monoester derivatives can be prepared directly.

Typical acylating agents useful in our process include anhydrides, halides and reactive esters of organic acids. When an acylating reagent contains functional groups which can themselves be acylated, such as an amino group, such groups must, of course, be protected by a suitable protecting group.

The temperature of the acylation reaction of this invention varies inversely with the reactivity of the acylating agent. With reactive acylating agents, such as acyl chlorides, the reaction is carried out at lower temperatures, such as from about −80° C. to about 0° C. A temperature of about −78° C. is preferred for such reactions. With less reactive acylating agents, such as anhydrides or reactive esters, the reaction is carried out at higher temperatures such as from about −20° C. to about room temperature.

An essential condition of the method of the present invention is that the acylation be carried out in the presence of an external base. External bases which are appropriate for this method are tertiary amines such as pyridine and 2,4,6-collidine. Sufficient external base is required to overcome the directing influence of the dimethylamino group at the 3'-position in OMT and DMT.

The reaction of the present invention is carried out until acylation of the 23-hydroxyl group is substantially complete. It will be recognized by those in the art that the reaction time will vary depending upon the conditions used, especially upon the reactivity of the acylating agent and the temperature at which the reaction is conducted.

Separation and purification of the desired 23-monoester derivatives of OMT or DMT are accomplished using procedures known in the art. Silica-gel chromatography is an especially useful technique for purifying the 23-monoesters of OMT and DMT.

In order to illustrate more fully the operation of this invention, the following examples are provided:

PREPARATION 1

Preparation of DMT

A. Shake-flask Fermentation of DMT

A lyophilized pellet of *Streptomyces fradiae* NRRL 12170 is dispersed in 1–2 ml of sterilized water. A portion of this solution (0.5 ml) is used to inoculate a vegetative medium (150 ml) having the following composition:

| Ingredient | Amount (%) |
| --- | --- |
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* NRRL 12170, preserved in 1-ml volumes in liquid nitrogen, is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
| --- | --- |
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DMT

In order to provide a larger volume of inoculum, 1200 ml of incubated vegetative medium, prepared in a manner similar to that described in section A, is used to inoculate 250 gallons of a second-stage vegetative growth medium having the following composition:

| Ingredient | Amount (%) |
| --- | --- |
| Corn steep liquor | 1.0 |
| Soybean oil meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |

Adjust pH to 8.5 with 50% NaOH solution.

This second-stage vegetative medium is incubated in a 350-gallon tank for about 48 hours at 28° C., with adequate aeration and agitation.

Incubated second-stage medium (144 gallons) thus prepared is used to inoculate 1000 gallons of sterile production medium having the following composition:

| Ingredient | Amount (%) |
| --- | --- |
| Fish meal | 0.875 |
| Corn meal | 1.5 |
| Corn gluten | 0.875 |
| CaCO$_3$ | 0.2 |
| NaCl | 0.1 |
| (NH$_4$)$_2$HPO$_4$ | 0.04 |
| Beet molasses | 2.0 |
| Soybean oil (crude) | 3.0 |
| Lecithin | 0.09 |
| Water | 91.32 |

Adjust pH to 7.2 with 50% NaOH solution.

The inoculated production medium is allowed to ferment in a 1600-gallon tank for 8 to 9 days at a temperature of 28° C. The fermentation medium is aerated with sterile air to keep the dissolved oxygen level between about 30% and 50% and is stirred with conventional agitators at about 250 rpm.

C. Isolation of DMT

Harvested whole broth (3800 L), obtained as described in Section B, is filtered, using a filter aid. The mycelial cake is washed with water; this water wash is added to the filtrate.

The pH of the filtrate is adjusted to pH 9.2, using a 50% aqueous solution of sodium hydroxide (9.5 L). The filtrate is extracted with ethyl acetate (2000 L). Deionized water (450 L) and sodium phosphate monobasic (6.4 kg) are added to the ethyl acetate extract with thorough mixing. The pH of this mixture is adjusted from about pH 6.0 to pH 4.35, using a phosphoric acid solution (3300 ml; 2 parts water to one part phosphoric acid). The aqueous phase is separated. The pH of the enriched aqueous phase is adjusted to pH 6.5 using a 50% aqueous sodium hydroxide solution (700 ml).

The resulting solution is concentrated to a volume of about 225 L under vacuum. The pH of the concentrated solution is adjusted to pH 9.2 by the addition of 10% aqueous sodium hydroxide (16 L). The resulting basic solution is permitted to stand overnight. The crystals which form are separated by fitration, washed with deionized water (50 L), and dried to give about 8.6 kg of product. The product thus obtained can be recrystallized from acetone-water.

PREPARATION 2

Preparation of OMT from DMT

DMT, prepared as described in Preparation 1, Section C, is dissolved in a dilute hydrochloric acid solution (final pH 1.8). The resulting solution is allowed to stand for 24 hours at room temperature and then is adjusted to pH 9.0 by the addition of sodium hydroxide. This basic solution is extracted with ethyl acetate, dichloromethane or chloroform. The extract is evaporated under vacuum to give OMT.

PREPARATION 3

Alternate Preparation of OMT from DMT

OMT is prepared from DMT by treating the DMT in the fermentation broth in which it is produced with mild acid as described in Preparation 2. Isolation of the OMT is accomplished by a procedure similar to that described from DMT in Section C of Preparation 1.

TLC Analysis

TLC analysis is conveniently carried out on silica gel, using an appropriate solvent system such as dichloromethane:methanol:conc. ammonium hydroxide (90:10:2) and UV light, anisaldehyde spray or iodine for detection.

EXAMPLE 1

Preparation of 23-O-Acetyl-OMT

OMT (5.0 g, 8.5 mmol) was dissolved in dichloromethane (100 ml) and 2,4,6-collidine (5ml), cooled in an acetone-dry ice bath and treated with acetyl chloride (0.75 ml, 10.6 mmol). The cold bath was removed and the mixture was stirred while allowing it to warm to room temperature over a 45-minute period. The mixture was washed with saturated NaHCO$_3$ solution, dried (Na$_2$SO$_4$) and filtered. The filtrate was evaporated under reduced pressure. The residue was chromatographed on silica gel (Waters Prep 500), eluting with a linear gradient of dichloromethane (4 liters) and 15% methanol in dichloromethane (4 liters). Fractions containing the desired product were located by TLC analysis, combined and evaporated to dryness to yield 1.83 g of 23-O-acetyl-OMT.

EXAMPLE 2

Preparation of 23-O-Phenylacetyl-OMT

OMT (3.0 g, 5.0 mmol) was dissolved in dichloromethane (50 ml) and 2,4,6-collidine (2.5 ml), cooled in an acetone-dry ice bath and treated with phenylacetyl chloride (0.83 ml, 6.3 mmol). The cold bath was removed, and the mixture was stirred while allowing it to warm to room temperature over a 30-minute period. The mixture was washed with saturated NaHCO$_3$ solution, dried (Na$_2$SO$_4$) and filtered. The filtrate was evaporated to dryness under reduced pressure. The residue was dissolved in a small volume of dichloromethane and purified by flash chromatography on silica gel (E. Merck 60), eluting with a linear gradient of dichloromethane (1 liter) and 15% methanol in dichloromethane (1 liter). Fractions containing the desired product were located by TLC analysis, combined and evaporated to dryness to yield 2.0 g (56%) of 23-O-phenylacetyl-OMT.

EXAMPLE 3

23-O-(Diphenylphosphoryl)-OMT

OMT (4.0 g, 6.7 mmol) was dissolved in dichloromethane (10 ml) and pyridine (1 ml), cooled in an acetone-dry ice bath and treated with diphenyl chlorophosphate (3.6 g, 13.4 mmol). The cold bath was removed, and the reaction was stirred and allowed to warm to room temperature over a 30-minute period. Since TLC analysis showed starting material was still present, the mixture was again cooled to −78° C., treated with diphenyl chlorophosphate (1.0 ml) and allowed to warm as before. The mixture was then washed with saturated NaHCO$_3$ solution, dried (Na$_2$SO$_4$) and filtered. The filtrate was evaporated under reduced pressure, diluted with dichloromethane-cyclohexane and re-evaporated. The crude product was purified by flash chromatography on silica gel (E. Merck 60), eluting with a linear gradient of dichloromethane (1 liter) and 15% methanol in dichloromethane (1 liter). Fractions containing the desired product were located by TLC analysis, combined and evaporated to dryness to yield 3.2 g (57%) of 23-O-diphenylphosphoryl-OMT.

EXAMPLE 4

23-O-Phenylacetyl-DMT

DMT (3.0 g, 4.05 mmol) was dissolved in dichloromethane (40 ml) and pyridine (1 ml) under an argon atmosphere. The solution was cooled to −78° C. in a dry ice-acetone bath, and phenylacetyl chloride (0.65 ml, 1.2 equiv) was added dropwise. After 5–10 minutes, the cooling bath was removed, and the reaction mixture was allowed to warm to room temperature over a 30-minute period. TLC analysis of an aliquot indicated that acylation of the 23-hydroxyl group was incomplete, so the reaction mixture was again cooled to −78° C., and treated with additional phenylacetyl chloride (0.45 ml). This procedure was repeated once again, with addition of further phenylacetyl chloride (0.35 ml) and pyridine (1 ml), to allow complete acylation of the 23-hydroxyl group (TLC analysis). The reaction mixture was worked up as described in Example 1. The crude product was purified by flash chromatography on silica gel, eluting with a linear gradient of dichloromethane (1 liter) and dichloromethane:methanol (85:15, 1 liter). Fractions containing the desired product were located by TLC, combined and evaporated to dryness to give 1.48 g (43%) of 23-O-phenylacetyl-DMT.

We claim:

1. In the method of preparing 23-monoester derivatives of an antibiotic selected from 5-O-mycaminosyl tylonolide and demycinosyltylosin, the improvement which consists of directly acylating the 23-hydroxyl group without protecting the remaining active groups in the antibiotic, said acylation being accomplished with an acylating agent selected from an acid chloride, an acid anhydride or a reactive ester in the presence of an external base at a temperature in the range of from −80° to room temperature until the 23-hydroxyl group of the antibiotic is acylated.

2. The method of claim 1 wherein the antibiotic is 5-O-mycaminosyl tylonolide.

3. The method of claim 1 wherein the antibiotic is demycinosyltylosin.

4. The method of claim 1 wherein the acylating agent is an acyl chloride and the reaction temperature is in a range of from about −80° C. to about 0° C.

5. The method of claim 1 wherein the acylating agent is an anhydride or reactive ester and the reaction temperature is in a range of from about −20° C. to about room temperature.

6. The method of claim 1 wherein the base is 2,4,6-collidine.

7. The method of claim 1 wherein the base is pyridine.

* * * * *